United States Patent [19]
Apelian et al.

[11] Patent Number: 5,284,989
[45] Date of Patent: Feb. 8, 1994

[54] OLEFIN OLIGOMERIZATION WITH SURFACE MODIFIED ZEOLITE CATALYST

[75] Inventors: Minas R. Apelian, Vincetown, N.J.; James R. Boulton, Chalfont; Anthony S. Fung, Chadds Ford, both of Pa.

[73] Assignee: Mobil Oil Corporation, Fairfax, Va.

[21] Appl. No.: 971,112

[22] Filed: Nov. 4, 1992

[51] Int. Cl.$^5$ .................................................. C07C 2/02
[52] U.S. Cl. .................................... 585/533; 585/520
[58] Field of Search ................................ 585/520, 533

[56] References Cited

U.S. PATENT DOCUMENTS

| | | | |
|---|---|---|---|
| 3,442,795 | 5/1969 | Kerr et al. | |
| 4,002,697 | 1/1977 | Chen. | |
| 4,088,605 | 5/1978 | Rollmann. | |
| 4,100,215 | 7/1978 | Chen. | |
| 4,101,595 | 7/1978 | Chen et al. | |
| 4,388,177 | 6/1983 | Bowes et al. | 208/111 |
| 4,520,221 | 5/1985 | Chen | 585/517 |
| 4,568,786 | 2/1986 | Chen et al. | 585/517 |
| 4,716,135 | 12/1987 | Chen | 502/62 |
| 4,788,375 | 11/1988 | Garwood et al. | 585/533 |
| 4,855,527 | 8/1989 | Page et al. | 585/533 |
| 4,870,038 | 9/1989 | Page et al. | 502/62 |
| 4,902,847 | 2/1990 | Juguin et al. | 585/533 |
| 5,004,841 | 4/1991 | Lee et al. | 585/453 |
| 5,043,307 | 8/1991 | Bowes et al. | 502/86 |
| 5,068,048 | 11/1991 | Chen et al. | 585/533 |
| 5,080,878 | 1/1992 | Bowes et al. | 423/328 |
| 5,757,191 | 10/1992 | Bowes et al. | 585/533 |

FOREIGN PATENT DOCUMENTS

0259526B1  3/1988  European Pat. Off. .

*Primary Examiner*—Patrick P. Garvin
*Assistant Examiner*—E. D. Irzinski
*Attorney, Agent, or Firm*—Alexander J. McKillop; Dennis P. Santini; Laurence P. Hobbes

[57] ABSTRACT

A method for producing substantially linear hydrocarbons by oligomerizing a lower olefin at elevated temperature and pressure which comprises contacting the lower olefin under oligomerization/polymerization conditions with constrained intermediate pore siliceous acidic zeolite, e.g., ZSM-22, -23 or -35, having Brönsted acid activity; wherein the zeolite has acidic pore activity and wherein the zeolite surface is rendered substantially inactive for acidic reactions. The zeolite surface can be inactivated by contact with dicarboxylic acid, e.g., oxalic acid. The olefin oligomers may be used as alkylating agents to prepare biodegradable alkylbenzenes and alkylphenylsulfonates.

20 Claims, No Drawings

OLEFIN OLIGOMERIZATION WITH SURFACE MODIFIED ZEOLITE CATALYST

BACKGROUND OF THE INVENTION

This application discloses a process for producing high molecular weight hydrocarbons from a lower olefin feedstock by employing a shape selective crystalline silicate catalyst which is surface inactivated.

Recent work in the field of olefin upgrading has resulted in a catalytic process for converting lower olefins to heavier hydrocarbons. Heavy distillate and lubricant range hydrocarbons can be synthesized over certain medium pore, shape-selective zeolite catalysts at elevated temperature and pressure to provide a product having substantially linear molecular conformations due to the ellipsoidal shape selectivity of such catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of ZSM-5 zeolite. Such a technique has been developed by Garwood, et al, as disclosed in European Patent Application No. 83301391.5, published 29 Sept. 1983. In U.S. Pat. Nos. 4,150,062; 4,211,640; 4,227,992; and 4,547,613 Garwood, et al disclose operating conditions for a process for selective conversion of $C_3$ + olefins to mainly aliphatic hydrocarbons.

In the process for catalytic conversion of olefins to heavier hydrocarbons by catalytic oligomerization using a medium pore shape selective acid crystalline zeolite, process conditions can be varied to favor the formation of hydrocarbons of varying molecular weight. At moderate temperature and relatively high pressure, the conversion conditions favor $C_{10}$ + aliphatic product. Lower olefinic feedstocks containing $C_2$-$C_8$ alkenes may be converted; however, the distillate mode conditions do not convert a major fraction of ethylene. A typical reactive feedstock consists essentially of $C_3$-$C_6$ mono-olefins, with varying amounts of non-reactive paraffins and the like being acceptable components.

Shape-selective oligomerization, as it applies to the conversion of $C_2$-$C_{10}$ olefins over ZSM-5, may produce higher olefins up to $C_{30}$ and higher. As reported by Garwood in "Intrazeolite Chemistry 23", (Amer. Chem. Soc., 1983), reaction conditions favoring higher molecular weight product are low temperature (200°-260° C.), elevated pressure (about 2000 kPa or greater), and long contact time (less than 1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of medium pore catalysts impose shape-selective constraints on the configuration of the large molecules, accounting for the differences with other catalysts.

The desired oligomerization-polymerization products include $c_{10}$ + substantially linear aliphatic hydrocarbons. This catalytic path for propylene feed provides a long chain which generally has lower alkyl (e.g., methyl) substituents along the straight chain.

The final molecular configuration is influenced by the pore structure of the catalyst. For the higher carbon numbers, the structure is primarily a methyl-branched straight olefinic chain, with the maximum cross-section of the chain limited by the dimension of the largest zeolite pore. Although emphasis is placed on the normal 1-alkenes as feedstocks, other lower olefins, such as 2-butene or isobutylene, are readily employed as starting materials due to rapid isomerization over the acidic zeolite catalysts. At conditions chosen to maximize heavy distillate and lubricant range products ($C_{20}$ +), the raw aliphatic product is essentially mono-olefinic. Overall branching is not extensive and may occur at spaced positions within the molecule.

The viscosity index of a hydrocarbon lube oil is related to its molecular configuration. Extensive branching in a molecule usually results in a low viscosity index. It is believed that two modes of oligomerization/polymerization of olefins can take place over acidic zeolites, such as HZSM-5. One reaction sequence takes place at Brönsted acid sites inside the channels or pores, producing essentially linear materials. The other reaction sequence occurs on the outer surface, producing more branched material. By decreasing the surface acid activity of such zeolites, fewer highly branched products with low VI are obtained.

Several techniques may be used to increase the relative ratio of intra-crystalline acid sites to surface active sites. This ratio tends to increase with crystal size due to geometric relationship between volume and superficial surface area. Deposition of carbonaceous materials by coke formation can also shift the effective ratio, as disclosed in U.S. Pat. No. 4,547,613.

Dealumination of zeolite surfaces can also reduce surface activity. Conventional techniques for zeolite dealumination include hydrothermal treatment, mineral acid treatment with HCl, $HNO_3$, and $H_2SO_4$, and chemical treatment with $SiCl_4$ or EDTA. The treatments are limited, in many cases, in the extent of dealumination by the onset of crystal degradation and loss of sorption capacity. U.S. Pat. No. 4,419,220 to LaPierre et al discloses that dealumination of zeolite Beta via treatment with HCl solutions is limited to $SiO_2/Al_2O_3$ ratios of about 200 to 300 beyond which significant losses to zeolite crystallinity are observed.

U.S. Pat. No. 3,442,795 to Kerr et al. describes a process for preparing highly siliceous zeolite-type materials from crystalline aluminosilicates by means of a solvolysis, e.g. hydrolysis, followed by a chelation. In this process, the acid form of a zeolite is subjected to hydrolysis, to remove aluminum from the aluminosilicate. The aluminum can then be physically separated from the aluminosilicate by the use of complexing or chelating agents such as ethylenediaminetetraacetic acid or carboxylic acid, to form aluminum complexes that are readily removable from the aluminosilicate. The examples are directed to the use of EDTA to remove alumina.

EP 0 259 526 B1 discloses the use of dealumination in producing zeolite ECR-17. The preferred dealumination method involves a combination of steam treatment and acid leaching, or chemical treatments with silicon halides. The acid used is preferably a mineral acid, such as HCl, $HNO_3$ or $H_2SO_4$, but may also be weaker acids such as formic, acetic, oxalic, tartaric acids and the like.

U.S. Pat. No. 4,388,177 to Bowes et al. discloses the preparation of a natural ferrierite hydrocracking catalyst by treatment with oxalic acid to impart catalytic activity for converting slightly branched as well as straight chain hydrocarbons in hydrodewaxing and naphtha upgrading. Increased activity is believed to arise from removal of iron, sodium and other impurities by such treatment.

It is known to use certain basic materials to deactivate the Brönsted acid sites on the surface of aluminosilicate catalysts. U.S. Pat. No. 4,520,221 and U.S. Pat. No. 4,568,786, Chen, et al., which are expressly incorporated herein disclose bulky amines, such as di-tert-butyl pyridine, as such basic materials.

U.S. Pat. No. 5,080,878 to Bowes et al., incorporated herein by reference, describes production of high viscosity index lubes by converting olefins over medium pore zeolites, e.g., ZSM-23, which are surface inactivated by contacting with aqueous fluorosilicate salt to replace external zeolite aluminum with silicon.

U.S. Pat. No. 4,870,038 to Page et al., which is expressly incorporated herein discloses the use of surface-inactivated zeolites such as ZSM-23 in olefin oligomerization processes which produce substantially linear hydrocarbons suitable for lubes or alkylating for preparing alkylbenzenes or alkylphenylsulfonates. The zeolites are surface-inactivated by contacting with bulky pyridine compound, e.g., 2,4,6-collidine.

The Young U.S. Pat. Nos. 4,301,316; 4,301,317; and 4,298,547, the entire disclosures of which are expressly incorporated by reference, disclose methods for using linear olefins, whereby these olefins are reacted with benzene in a particular way and then sulfonated to form biodegradable alkylbenzene sulfonic acid based detergents, particularly 2-phenylalkane sulfonates.

SUMMARY OF THE INVENTION

The present invention provides a process for producing substantially linear hydrocarbons by oligomerizing a lower olefin at elevated temperature and pressure. The process comprises contacting the lower olefin under polymerization conditions with a catalyst comprising a siliceous acidic zeolite having Brönsted acid activity, sorbing 10 to 40 mg 3-methylpentane at 90° C., 90 torr, per g dry zeolite when in the hydrogen form, wherein the zeolite has acidic pore activity and wherein the zeolite surface is rendered substantially inactive for acidic reactions by having been contacted with dicarboxylic acid under conditions sufficient to effect a significant reduction in surface acidity of the zeolite as determined by tri-tertiarybutylbenzene conversion without substantially reducing the overall activity of the zeolite as indicated by alpha value.

According to another aspect of this application, there is provided a process for producing substantially linear hydrocarbons by oligomerizing a lower olefin at elevated temperature and pressure which comprises contacting the lower olefin under polymerization conditions with acidic aluminosilicate ZSM-23 zeolite having Brönsted acid activity; wherein the zeolite has acidic pore activity and wherein the zeolite surface is rendered substantially inactive for acidic reactions by contacting with oxalic acid under conditions sufficient to effect a significant reduction in surface acidity of the zeolite as determined by tri-tertiarybutylbenzene conversion.

Said contacting of lower olefin is carried out at temperatures less than 260° C., weight hourly space velocities less than 1; and pressures of at least 2000 kPa, preferably at temperatures of 170° to 240° C., weight hourly space velocities of 0.05 to 0.40; and pressures of 5200 to 11000 kPa, for example, temperatures of 190° to 220° C., weight hourly space velocities of 0.1 to 0.3; and pressures of 6200 to 7600 kPa.

According to another aspect of the invention, there is provided a multi-stage process for producing high viscosity index lubricating oils from lower olefin feed which comprises contacting the lower olefins in a primary reaction zone under conditions of elevated temperature and pressure with a siliceous acidic ZSM-23 zeolite having Brönsted acid activity; wherein said zeolite has acidic pore activity and wherein the zeolite surface is rendered substantially inactive for acidic reactions by contacting with oxalic acid under conditions sufficient to effect a significant reduction in surface acidity of the zeolite as determined by tri-tertiarybutylbenzene conversion, to produce substantially linear $C_{10}$ + intermediate olefins; and contacting at least a portion of the primary stage effluent in a secondary reaction zone with an acid catalyst to effectively polymerize the $C_{10}$ + hydrocarbons.

Finally, in yet another aspect of the invention there is provided a process for the selective alkylation of an aromatic compound with a relatively long chain length alkylating agent to produce substantially linear phenylalkanes, said alkylating agent comprising a mixture of mono-olefins having 12 carbon atoms, said mono-olefins having a straight backbone chain of at least 10 carbon atoms, said mono-olefins having an average of from 0.40 to 2.00 methyl side groups per carbon chain, said mono-olefins comprising at least 5 mole percent of dodecene, at least 30 mole percent methylundecene and at least 5 mole percent dimethyldecene; said process comprising contacting said aromatic compound with said alkylating agent in the presence of a siliceous acidic ZSM-23 zeolite having Brönsted acid activity; wherein said zeolite has acidic pore activity and wherein the zeolite surface is rendered substantially inactive for acid catalyzed reactions by contacting with oxalic acid under conditions sufficient to effect a significant reduction in surface acidity of the zeolite as determined by tri-tertiarybutylbenzene conversion, under sufficient reaction conditions. The resulting phenylalkane can, in turn, be converted to an alkylbenzene sulfonate by a process comprising sulfonating the phenylalkane.

The present invention is particularly useful in that a dicarboxylic acid treatment of the zeolite employed provides a catalyst of significantly enhanced catalyst activity for olefin conversion to substantially linear hydrocarbons. The treatment with dicarboxylic acid selectively deactivates the surface acidity of the zeolite without substantially reducing the alpha value (as hereinafter described) or overall activity of the zeolite, resulting in reduced catalyst aging.

Catalyst

The preferred catalysts, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

Pore Size Index

| Type | Largest Ring Size | Zeolite | Axes of Largest Channel, A | Pore Size Index |
|---|---|---|---|---|
| 1 | 8 | Chabazite | 3.8 × 3.8 | 14.4 |
| | | Erionite | 3.6 × 5.1 | 18.4 |
| | | Linde A | 4.1 × 4.1 | 16.8 |
| 2 | 10 | ZSM-22 | 4.4 × 5.5 | 24.2 |
| | | ZSM-23 | 4.5 × 5.2 | 23.4 |
| | | ZSM-35 | 4.2 × 5.4 | 22.7 |
| | | ALPO-11 | 3.9 × 6.3 | 24.6 |
| 3 | 10 | ZSM-5 | 5.3 × 5.6 | 29.1 |
| | | ZSM-11 | 5.3 × 5.4 | 28.6 |
| | | Stilbite | 4.9 × 6.1 | 29.9 |
| | | ZSM-57 (10) | 5.1 × 5.8 | 29.6 |
| 4 | 12 | ZSM-12 | 5.5 × 5.9 | 32.4 |
| | | Mordenite | 6.5 × 7.0 | 45.5 |
| | | Beta (C-56) | 6.2 × 7.7 | 47.7 |
| | | Linde-L | 7.1 × 7.1 | 50.4 |
| | | Mazzite (ZSM-4) | 7.4 × 7.4 | 54.8 |
| | | ALPO$_4$-5 | 7.3 × 7.3 | 53.3 |

It can be seen that small pore, eight-ring zeolites have a Pore Size Index below about 20, the intermediate pore, 10-ring zeolites of about 20–31, and large pore, 12-ring zeolites above about 31. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolites useful for this invention are those of Type 2 with a Pore Size Index of 20–26.

The Type 2 zeolites are distinguished from the other types by their sorption characteristics towards 3-methylpentane. Representative equilibrium sorption data and experimental conditions are listed in Table B.

Type 2 zeolites sorb in their intracrystalline voids at least about 10 mg and less than about 40 mg of 3-methylpentane at 90° C., 90 torr 3-methylpentane, per gram dry zeolite in the hydrogen form. In contrast, Type 3 zeolites sorb greater than 40 mg 3-methylpentane under the conditions specified.

The equilibrium sorption are obtained most conveniently in a thermogravimetric balance by passing a stream of inert gas such as helium containing the hydrocarbon with the indicated partial pressure over the dried zeolite sample held at 90° C. for a time sufficient to obtain a constant weight.

Samples containing cations such as sodium or aluminum ions can be converted to the hydrogen form by well-known methods such as exchange at temperatures between 25° and 100° C. with dilute mineral acids, or with hot ammonium chloride solutions followed by calcination. For mixtures of zeolites with amorphous material or for poorly crystallized samples, the sorption values apply only to the crystalline portion.

This method of characterizing the Type 2 zeolites has the advantage that it can be applied to new zeolites whose crystal structure has not yet been determined.

TABLE B

Equilibrium Sorption Data of Medium Pore Zeolites

| Type | Zeolite | Amount sorbed, mg per g zeolite 3-Methylpentane[a] |
|---|---|---|
| 2 | ZSM-22 | 20 |
| | ZSM-23 | 25 |
| | ZSM-35 | 25 |
| 3 | ZSM-5 | 61 |
| | ZSM-12 | 58 |
| | ZSM-57 | 70 |
| | MCM-22 | 79 |

[a] at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent is described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

ZSM-23 is more particularly described in U.S. Pat. No. 4,076,842, the entire contents of which are incorporated herein by reference. For purposes of the present invention, ZSM-23 is considered to include its isotypes, e.g., EU-13, ISI-4, and KZ-1.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D. An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974).

The zeolite catalyst used is preferably at least partly in the hydrogen form, e.g., HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500p20 C. for 1 hour or more. The hydrogen form can then be obtained by base exchange with ammonium salts followed by calcination, e.g., at 500° C. in air. Acid treatment may result in dealumination and is therefore not typically practiced. Other cations, e.g. metal cations, can be introduced by conventional base exchange or impregnation techniques.

The zeolite may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant processes. The relative proportions of finely divided zeolite and inorganic oxide gel matrix vary widely with the zeolite content ranging from about 1 to about 90 percent by weight and more usually in the range of about 30 to about 80 percent by weight of the composite.

The regeneration of spent zeolite catalytt used in the oligomerization reaction is carried out oxidatively or hydrogenatively employing procedures known in the art.

In order to obtain desired olefin oligomerization activity/selectivity, the zeolite, preferably in the hydrogen form, should have an alpha value between about 5 and 400, preferably between about 10 and 100 when used in the catalyst of the present invention. Alpha value, or alpha number, of a zeolite is a measure of zeolite acidic functionality and is more fully described together with details of its measurement in U.S. Pat. No. 4,016,218, *J. Catalysis*, 6, pp. 278-287 (1966) and *J. Catalysis*, 61, pp. 390-396 (1980). The experimental conditions cited in the latter reference are used for characterizing the catalysts described herein.

The surface acidity of the catalyst can be determined by conversion of tri-tertiarybutylbenzene, a bulky molecule that can only react with the acid sites on the zeolite crystal surface. Dealkylation of TTBB is a facile, reproducible method for measuring surface acidity of catalysts. External surface acidity can be measured exclusive of internal activity for zeolites with pore diameters up to and including faujasite. As a test reaction, dealkylation of TTBB occurs at a constant temperature in the range of from 25° to 300° C. and preferably in the range of from about 200° to 260° C.

The experimental conditions for the test used herein include a temperature of 200° C. and atmospheric pressure. The dealkylation of TTBB is carried out in a glass reactor (18 cm ×1 cm OD) containing an 8 g 14/30 Vycor TM chip preheater followed by 0 0.1 g catalyst powder mixed with Vycor TM chips. The reactor is heated to 200° C. in 30 cc/g nitrogen for 30 minutes to remove impurities from the catalyst sample. Ten g/ hr of TTBB dissolved in toluene (7% TTBB) is injected into the reactor. The feed vaporizes as it passes through the preheater and passes over the catalyst sample as vapor. After equilibrium is reached the nitrogen is switched to 20 cc/min hydrogen. The test is then run for 30 minutes with the reaction products in a cold trap.

The reaction products are analyzed by gas chromatography. The major dealkylation product is di-t-butylbenzene (DTBB). Further dealkylation to t-butylbenzene (TBB) and benzene (B) occurs but to a lesser extent.

Conversion of TTBB is calculated on a molar carbon basis. Dealkylation product weight %s are each multiplied by the appropriate carbon number ratio to convert to the equivalent amount of TTBB, i.e. DTBB ×18/14, TBB ×18/10 and B ×18/6. These values are then used in the following conversion equation where asterisks indicate adjustment to the equivalents.

$$\% \text{ Conversion} = \frac{DTBB^* + TBB^* + B^*}{TTBB + DTBB^* + TBB^* + B^*} \times 100$$

In addition, thermal background experiments using reactors filled with Vycor TM chips only show no TTBB conversion due to Vycor TM or other reactor components.

Limiting surface acidity of the above catalysts is desirable for preventing undesired reactions on the zeolite surface which are not subject to the shape-selective constraints imposed upon those reactions occurring within the zeolite interior. However, reducing the surface acidity will generally effect a reduction in overall activity of the zeolite. In one aspect, the present invention relates to the treatment of the zeolite which is contacted with dicarboxylic acid under conditions resulting in a reduction in surface acidity (as measured by tri-tertiarybutylbenzene conversion) of at least 20%, preferably at least 50%, more preferably at least 75%, without a significant reduction in overall activitt as measured by alpha test. By significant reduction in overall activity is meant a reduction in alpha value of not greater than 20%.

The surface acidity of the zeolite can be reduced by dealumination of the zeolite surface. Performance measures typically improved by dealumination include product selectivity, product quality and catalyst stability.

The present invention provides a process for the selective dealumination of the zeolite used in oligomerization of olefins at the zeolite crystal surface by contacting the zeolite with dicarboxylic acid. The treatment with dicarboxylic acid is believed to remove aluminum from the crystal surface of the zeolite.

Prior to or following contact with dicarboxylic acid, the zeolite may be composited with a porous matrix material, such as alumina, silica, titania, zirconia, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Suitable dicarboxylic acids for use in the process of this invention include oxalic, malonic, succinic, glutaric, adipic, citric, tartaric, maleic, phthalic, isophthalic, terephthalic, fumaric or mixtures thereof. Oxalic acid is preferred. The dicarboxylic acid may be used in solution, such as an aqueous dicarboxylic acid solution.

Generally, the acid solution has a concentration in the range from about 0.01 to about 4M. Preferably, the acid solution concentration is in the range from about 1 to about 3M.

The dicarboxylic acid is generally in a volume solution to volume catalyst ratio of at least about 1:1, preferably at least about 4:1.

Treatment time with the dicarboxylic acid solution is as long as required to provide the desired reduction in surface acidity. Generally the treatment time is at least about 10 minutes. Preferably, the treatment time is at least about 1 hour.

More than one dicarboxylic acid treatment step may be employed in the process of the present invention for enhanced deactivation of surface acidity.

The treatment temperature is generally in the range from about 32° F. to about reflux. Preferably, the treatment temperature is from about 15° C. to 93° C. (60° F. to 200° F.), and more preferably from 49° C. to 82° C. (120° F. to 180° F.).

The dicarboxylic acid treatment may also be combined with other dealumination techniques, such as steaming and chemical treatment.

While not wishing to be bound by theory, it is believed that the dicarboxylic acid combines with aluminum in the treated zeolite to form an aluminum-containing species which is larger than the zeolite surface pore openings of constrained medium pore zeolites. This results in dealumination only at the surface of these zeolites.

EMBODIMENTS

It has been discovered that when a dicarboxylic acid-treated, surface-inactivated, but internally active, constrained medium pore size ZSM-23 metallosilicate zeolite catalyst, e.g., ZSM-23, is employed in olefin oligomerization, the reaction yields a high quality, essentially linear oligomer stock which can, inter alia, be efficiently converted to high VI lube oils.

Unless otherwise specified, metric units and parts-by-weight (pbw) are utilized in the description and examples.

When propylene or butene are oligomerized according to processes described herein, a mixture of liquid hydrocarbon products are formed. More particularly, this mixture of hydrocarbons may comprise at least 95% by weight of mono-olefin oligomers of the empirical formula

$$C_{(n+nm)}H_{2(n+nm)}$$

where n is 3 or 4 and m is an integer from 1 to 6, said mono-olefin oligomers comprising at least 20 percent by weight of olefins having at least 12 carbon atoms, said olefins having at least 12 carbon atoms having an average of from 0.80 to 2.00 methyl side groups per carbon chain, said olefins not having any side groups other than methyl.

It will be understood that methyl side groups are methyl groups which occupy positions other than the terminal positions of the first and last (i.e., alpha and omega) carbon atoms of the longest carbon chain. This longest carbon chain is also referred to herein as the straight backbone chain of the olefin. The average number of methyl side groups for the $C_{12}$ + olefins may comprise any range within the range of 0.80 to 2.00, e.g., from 0.80 to 1.90, e.g., from 0.80 to 1.80, e.g. from 0.80 to 1.70, e.g., from 0.80 to 1.60, e.g., from 0.80 to 1.50, e.g., from 0.80 to 1.40, e.g., from 0.80 to 1.30, etc.

Preferably the branching target is 1.3 to 1.7 methyls/$C_{12}$, e.g. 1.3 to 1.6 methyls/$C_{12}$.

These oligomers may be separated into fractions by conventional distillation separation. When propylene is oligomerized, olefin fractions containing the following numbers of carbon atoms can be obtained: 6, 9, 12, 15, 18 and 21. When butene is oligomerized, olefin fractions containing the following numbers of carbon atoms may be obtained: 8, 12, 16, 20, 24 and 28. It is also possible to oligomerize a mixture of propylene and butene and to obtain a mixture of oligomers having at least 6 carbon atoms.

By fractionating an oligomerization product prepared by processes described herein, one may obtain a mixture of hydrocarbons, said hydrocarbons comprising at least 95 (e.g., at least 98) percent by weight of mono-olefins having 12 carbon atoms, said mono-olefins having a straight backbone chain of at least 10 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{12}$ olefins may comprise or consist essentially of at least 5 (e.g., from 5 to 40, e.g., from 5 to 25) mole percent dodecene (i.e., a $C_{12}$ olefin having no methyl side groups) at least 30 (e.g., from 30 to 90, e.g., from 65 to 80) mole percent methylundecene (i.e., a $C_{12}$ olefin having one methyl side group) and at least 5 (e.g., from 5 to 40, e.g., from 5 to 25) mole percent dimethyldecene (i.e., a $C_{12}$ olefin having two methyl side groups).

Another hydrocarbon fractionation product may be a mixture of hydrocarbons, said hydrocarbons comprising at least 95 (e.g., at least 98) percent by weight of mono-olefins having 15 carbon atoms, said mono-olefins having a straight backbone chain of at least 13 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{15}$ olefins may comprise or consist essentially of at least 5 (e.g., from 5 to 40, e.g., from 5 to 25) mole percent pentadecene (i.e., a $C_{15}$ olefin having no methyl side groups) at least 30 (e.g., from 30 to 90, e.g., from 65 to 80) mole percent methyltetradecene (i.e., a $C_{15}$ olefin having one methyl side group) and at least 5 (e.g., from 5 to 40, e.g., from 5 to 25) mole percent dimethyltridecene (i.e., a $C_{15}$ olefin having two methyl side groups).

Another hydrocarbon fractionation product may be a mixture of hydrocarbons, said hydrocarbons comprising at least 95 (e.g., at least 98) percent by weight of mono-olefins having 16 carbon atoms, said mono-olefins having a straight backbone chain of at least 14 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{16}$ olefins may comprise or consist essentially of at least 5 (e.g., from 5 to 40, e.g., from 5 to 25) mole percent hexadecene (i.e., a $C_{16}$ olefin having no methyl side groups) at least 30 (e.g., from 30 to 90, e.g., from 65 to 80) mole percent methylpentadecene (i.e., a $C_{16}$ olefin having one methyl side group) and at least 5 (e.g., from 5 to 40, e.g., from 5 to 25) mole percent dimethyltetradecene (i.e., a $C_{16}$ olefin having two methyl side groups).

Another hydrocarbon fractionation product may be a mixture of hydrocarbons, said hydrocarbons comprising at least 95 (e.g., at least 98) percent by weight of mono-olefins having 18 carbon atoms, said mono-olefins having a straight backbone chain of at least 16 carbon atoms, said mono-olefins having an average of from 0.40 to 2.00 (e.g., from 0.50 to 1.90, e.g., from 0.60 to 1.80, e.g., from 0.70 to 1.70, e.g., from 0.80 to 1.60, e.g., from 0.80 to 1.50, e.g., from 0.80 to 1.40, e.g., from 0.80 to 1.30) methyl side groups per carbon chain. These $C_{18}$ olefins may comprise or consist essentially of at least 5 (e.g., from 5 to 40, e.g., from 5 to 25) mole percent octadecene (i.e., a $C_{18}$ olefin having no methyl side groups) at least 30 (e.g., from 30 to 90, e.g., from 65 to 80) mole percent methylheptadecene (i.e., a $C_{18}$ olefin having one methyl side group) and at least 5 (e.g., from 5 to 40, e.g., from 5 to 25) mole percent dimethylhexadecene (i.e., a $C_{18}$ olefin having two methyl side groups).

These olefin mixtures, particularly the above-mentioned fractionation products, may be used as is or may be blended with other olefins such as various straight chain olefins (i.e. olefins having no methyl side groups) to provide further olefin mixtures.

One use for olefin oligomers descried herein, particularly $C_{12}$ fractions of the oligomers, is as alkylating agents in a process for the selective alkylation of an aromatic compound (e.g., benzene) with a relatively long chain length alkylating agent to produce substantially linear phenylalkanes. Catalysts and reaction conditions for this alkylation process are disclosed in the aforementioned U.S. Pat. No. 4,301,317, which describes a similar alkylation process using linear olefins (e.g., dodecene) as alkylating agents.

The reaction of aromatic compounds with the present long-chain oligomers, when carried out in the presence of certain crystalline zeolite materials as catalysts, will result in linear phenylalkanes in which the content of the 2-phenyl substituted linear alkane isomer is believed to be in excess of its expected equilibrium concentration. The crystalline zeolites utilizable in this process are characterized by channels or networks of pores therethrough, the major dimension of the opening to the channels or networks of pores being between about 6 angstrom units and about 7 angstrom units. Specific preferred catalysts include cancrinite, gmelinite, mordenite, and offretite and synthetic and naturally occurring isotypes thereof. A particularly preferred zeolite is dealuminized mordenite.

The alkylation process is carried out by contacting the aromatic compound, which may be a substituted or unsubstituted benzene, with the alkylating agent in the presence of the specified type of zeolite catalyst and under suitable alkylation conditions. Preferred conditions include a temperature of between about 50° C. and 500° C. and a pressure of about $2.5 \times 10^4$ N/m² to $2.5 \times 10^7$ N/m² (0.25-250 atmospheres).

The aromatic compounds which are to be reacted with the foregoing alkylating agents to yield phenylalkanes by the process disclosed herein are benzene compounds. These benzene compounds may be unsubstituted, or they may carry from 1 to 2 substituents on the ring structure. If substituted, the substituent may be an alkyl group having from 1 to 10 carbon atoms therein, or may be a halide, an alkoxy, an aryl group, and so forth or any combination of such substituents.

The zeolites useful in the alkylation process generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

An especially useful modifyng treatment entails steaming of the zeolite by contact with an atmosphere containing from about 5 to about 100 percent steam at a temperature of from about 250° to 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

In practicing the desired alkylation process, it may be useful to incorporate the above-described intermediate pore size crystalline zeolites in another material resistant to the temperature and other conditions employed in the process. Such matrix materials include synthetic or naturally occurring substances as well as inorganic materials such as clay, silica, and/or metal oxides. The latter may be either naturally occurring or in the form of gels or gelatinous precipitates including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

The alkylation process is conducted such that the organic reactants, i.e., the aromatic compound and the alkylating agent, are brought into contact with the zeolite in a suitable reaction zone, such as for example a fixed bed of the catalyst, under effective alkylation conditions. Such conditions include a temperature of between about 50° C. and about 500° C., a pressure of between about $2.5 \times 10^4$ N/m² and about $2.5 \times 10^7$ N/m² (0.25-250 atmospheres), and a feed weight hourly space velocity (WHSV) of between about 0.1 and about 500. The latter WHSV is based upon the weight of the catalyst compositions employed, i.e. the total weight of active catalyst and binder therefor. Preferred reaction conditions include a temperature within the approximate range of 100° C. to 350° C. with a feed WHSV of between 0.5 and 100. Although the reaction normally takes place at atmospheric pressure ($10^5 N/m^2$), the preferred pressure range extends from about $10^5 N/m^2$ to about $5 \times 10^6 N/m^2$. The reactants may be in either the vapor phase or the liquid phase and may be neat, i.e., free from intentional admixture or dilution with other material, or may be brought into contact with the zeolite with the aid of carrier gases or diluents such as, for example, hydrogen or nitrogen.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The alkylbenzenes prepared by the above-discussed alkylation process are useful as intermediates for the production of alkylphenylsulfonates, which are useful as detergents or surfactants. Processes for sulfonating alkylbenzenes are described in the aforementioned U.S. Pat. No. 4,298,547. More particularly, alkylbenzenes may be converted to alkylphenylsulfonates by sulfonation of the aromatic ring with sulfuric acid. The reaction is well known in the art and is commonly carried out by contacting the organic compound with sulfuric acid at temperatures of from about $-70°$ C. to about $+60°$ C. Detailed descriptions of specific commercial processes abound in the literature—see, for instance, pages 60-62 of INDUSTRIAL CHEMICALS, Third Edition, by W. L. Faith et al, published by John Wiley & Sons, Inc., 1966—and those skilled in the field need only refer to the conventional literature for instruction on how to carry out such reactions.

The following examples illustrate the process of the present invention.

Example 1

Preparation of ZSM-23

ZSM-23 was prepared by charging 85.5 parts water to an autoclave followed by 2.64 parts KOH solution (45% by weight), 1.0 part aluminum sulfate (17.2% $Al_2O_3$) and 0.5 parts ZSM-23 seeds (100% basis). After mixing thoroughly, 14.5 parts of Ultrasil VN3 precipitated silica (Nasilco), then 5.1 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, washed, filtered and dried. 65 parts of the dried ZSM-23 were combined with 35 parts of $SiO_2$ (Hi-Sil, a product of PPG Industries Chemical Division, dry mulled and extruded to form 1/16 inch pellets which were dried at 120° C. The pellets were then calcined in flowing nitrogen for 2 hours at 538° C. and 3 hours in air at the same temperature. The cooled catalyst was exchanged with 1 N $NH_4NO_3$ (5 cc/g catalyst) at room temperature for one hour then washed with water. The exchange procedure was repeated and the catalyst dried at 120° C. The exchanged extrudate was then calcined at 538° C. in flowing air for 3 hours. The resulting catalyst exhibited an alpha activity of 27 and a surface acidity of 4.6.

Example 2

Surface Acidity Reduction

A sample of ZSM-23 from Example 1 was treated with 2M oxalic acid at 71° C. for one hour. The treated sample was washed with water, dried at 150° C. for 8 hours, and calcined at 375° C. for 3 hours. The resulting catalyst had an alpha value of 33 and a surface acidity of 2.1. While the change in alpha value is within the accuracy of the alpha test, the reduction in surface acidity represents a significant decrease.

Example 3

Surface Acidity Reduction

A second sample of ZSM-23 from Example 1 was treated with 2 M oxalic acid at 71° C. for two hours. The treated sample was washed with water, dried at 150° C. for 8 hours, and calcined at 375° C. for 3 hours. The resulting catalyst had an alpha value of 29 and a surface acidity less than 0.1.

Example 4

Surface Acidity Reduction with Collidine

A third sample of 7.7 g of the ZSM-23 catalyst from Example 1 having a silica/alumina ratio of 110:1 was treated with 0.059 g collidine/g of catalyst by contacting the catalyst with a dilute collidine-pentane solution containing 0.0454 g collidine which is an amount sufficient to poison 25% of acid sites present in the zeolite component of the catalyst. The collidine adsorbed very rapidly and completely to the catalyst. The catalyst was dried slowly and then purged with nitrogen.

Example 5

Oligomerization Propylene with ZSM-23 at 225° C.

The catalysts of Examples 1, 2, 3 and 4 were evaluated in a semi-batch autoclave for activity, product selectivity, and product structure with propylene feed on demand for five hours at 800 psig and 225° C. Under the above conditions, unmodified ZSM-23 catalyst of Example 1 typically yielded 38 g/hr of liquid product with an average methyl branching of 1.9 methyl branches per $C_{12}$. Collidine-modified ZSM-23 catalyst of Example 4 typically yielded 16 g/hr of liquid product with an average methyl branching of 1.3 methyl branches per $C_{12}$. The semi-batch evaluation is reproducible to $\pm 2$ g/hr of liquid product.

A sample of ZSM-23 catalyst of Example 3 was evaluated in a semi-batch autoclave under typical oligomerization conditions of 225° C., 800 psig for 5 hours. The catalyst yielded 109 g/hr of liquid product that had an average methyl branching of 1.5 branches per $C_{12}$. The activity of the oxalic acid treated catalyst was over three times the unmodified ZSM-23 and over six times that of the collidine modified ZSM-23 catalyst of Example 4. Product methyl branching of the oxalic acid treated catalyst was within the branching target of 1.3 to 1.7 methyls/$C_{12}$ necessary for preparing desirable chemical intermediates. The oxalic acid treated catalyst did not require treatment with collidine to achieve the desired product quality.

The determination of Branching Index is a useful and sensitive method practiced by those skilled in the arts to which the present invention applies and used to quantitatively assess the degree of linearity of a molecule or molecular mixture. The index is determined as follows: the C6 and C9 oligomers are first removed from the sample and the C12+ fraction is hydrogenated using Pd/charcoal catalyst in acetic acid. The hydrogenated sample is extracted from the acetic acid into deuterochloroform and the 1H NMR spectrum determined. The branching index is defined as the ratio of the intensity (area) of the resonance due to CH3 (0.7-1.0 ppm) divided by the sum of the intensities (areas) of the resonances due to CH3 (0.7.-1.0 ppm) and CH2 (1.1-1.8 ppm). The number of methyl groups per molecule is defined by the equation $$Me/molecule = B.I.*(n+1))/150$$

where

B. I.=branching index as defined above and n=carbon number of the fraction of interest.

This calculated number of methyls per molecule includes the two terminal methyl groups. Therefore, to determine the actual number of methyl side groups, e.g., mid-chain methyl groups, these two terminal methyl groups must be subtracted from the total methyl/molecule value calculated.

While the instant invention has been described by specific examples and embodiments, there is no intent to limit the inventive concept except as set forth in the following claims.

What is claimed is:

1. A method for producing substantially linear hydrocarbons by oligomerizing/polymerizing a lower olefin at elevated temperature and pressure which comprises
   contacting the lower olefin under oligomerization/polymerization conditions with a catalyst comprising a siliceous acidic zeolite having Brönsted acid activity, capable of sorbing 10 to 40 mg 3-methylpentane at 90° C., 90 torr, per g dry zeolite when in the hydrogen form, wherein said zeolite has acidic pore activity and wherein the zeolite surface is rendered substantially inactive for acidic reactions by having been contacted with dicarboxylic acid under conditions sufficient to effect a reduction of at least 20% in surface acidity of the zeolite as determined by tri-tertiarybutylbenzene conversion without substantially reducing the overall activity of the zeolite as indicated by alpha value.

2. The method of claim 1 wherein said contacting of lower olefin is carried out at temperatures less than 260° C., weight hourly space velocities less than 1; and pressures of at least 2000 kPa.

3. The method of claim 1 wherein said contacting of lower olefin is carried out at temperatures of 170° to 240° C., weight hourly space velocities of 0.05 to 0.40; and pressures of 5200 to 11000 kPa.

4. The method of claim 1 wherein said contacting of lower olefin is carried out at temperatures of 190° to 220° C., weight hourly space velocities of 0.1 to 0.3; and pressures of 6200 to 7600 kPa.

5. The method of claim 1 wherein said zeolite is selected from the group consisting of those having the framework structure of ZSM-22, ZSM-23, and ZSM-35.

6. The method of claim 1 wherein said zeolite is ZSM-22.

7. The method of claim 1 wherein said zeolite is ZSM-23.

8. The method of claim 1 wherein said zeolite is ZSM-35.

9. The method of claim 1 wherein said catalyst comprises 10 to 99 wt % of a refractory inorganic oxide binder.

10. The method of claim 1 wherein said catalyst comprises 20 to 70 wt % of a silica binder.

11. The method of claim 1 wherein said surface acidity is reduced by at least 50%.

12. The method of claim 1 wherein said contacting with dicarboxylic acid results in less than about 10% loss of crystallinity.

13. The method of claim 1 wherein said dicarboxylic acid is contained in an aqueous dicarboxylic acid solution.

14. The method of claim 1 wherein said dicarboxylic acid is in a concentration in the range of from about 0.01 to about 4M.

15. The method of claim 1 wherein said dicarboxylic acid is selected from the group consisting of oxalic, malonic, succinic, glutaric, adipic, maleic, phthalic, isophthalic, terephthalic, fumaric, tartaric and mixtures thereof.

16. The method of claim 1 wherein said dicarboxylic acid is oxalic acid.

17. The method of claim 1 wherein said contacting of lower olefin is for a time of at least about 10 minutes, at a temperature in the range of 15° C. to 93° C. (60° F. to 200° F.).

18. The method of claim 1 wherein said lower olefin comprises $C_3$ to $C_6$ olefin.

19. A method for producing substantially linear hydrocarbons by oligomerizing/polymerizing a lower olefin at elevated temperature and pressure which comprises
   contacting the lower olefin under oligomerization/polymerization conditions with acidic aluminosilicate ZSM-23 zeolite having Brönsted acid activity; wherein said zeolite has acidic pore activity and wherein the zeolite surface is rendered substantially inactive for acidic reactions by contacting with oxalic acid under conditions sufficient to effect a reduction of at least in surface acidity of the zeolite as determined by tri-tertiarybutylbenzene conversion.

20. A multi-stage method for producing high viscosity index lubricating oils from lower olefin feed which comprises
   contacting the lower olefins in a primary reaction zone under conditions of elevated temperature and pressure with a siliceous acidic ZSM-23 zeolite having Brönsted acid activity; wherein said zeolite has acidic pore activity and wherein the zeolite surface is rendered substantially inactive for acidic reactions by contacting with oxalic acid under conditions sufficient to effect a reduction of at least 20% in surface acidity of the zeolite as determined by tri-tertiarybutylbenzene conversion, to produce substantially linear $C_{10}$ + intermediate olefins; and
   contacting at least a portion of the primary stage effluent in a secondary reaction zone with an acid catalyst to effectively polymerize the $C_{10}$ + hydrocarbons.

* * * * *

UNITED STATES PATENT AND TRADEMARK OFFICE
CERTIFICATE OF CORRECTION

PATENT NO. : 5,284,989
DATED : February 8, 1994
INVENTOR(S) : Minas R. Apelian et al It is certified that error appears in the above-indentified patent and that said Letters Patent is hereby corrected as shown below:

Col. 16, line 45 (claim 19), after "least" insert --20%--.

Signed and Sealed this

Seventh Day of February, 1995

Attest:

BRUCE LEHMAN

Attesting Officer          Commissioner of Patents and Trademarks